United States Patent
Naidu (12)

(10) Patent No.: US 6,384,201 B1
(45) Date of Patent: May 7, 2002

(54) SYNTHETIC METHOD FOR THE PREPARATION OF THE ANTINEOPLASTIC AGENT ETOPOSIDE

(75) Inventor: Ragina Naidu, Vancouver (CA)

(73) Assignee: Phytogen Life Sciences Inc., Delta (CA)

( * ) Notice: Subject to any disclaimer, the term of this patent is extended or adjusted under 35 U.S.C. 154(b) by 0 days.

(21) Appl. No.: 09/565,228

(22) Filed: May 4, 2000

Related U.S. Application Data

(63) Continuation of application No. 09/150,879, filed on Sep. 10, 1998, now abandoned.

(51) Int. Cl.[7] .................. C07H 15/24; C07H 15/00; C07H 1/00; C07H 1/06
(52) U.S. Cl. .............. 536/18.6; 536/4.1; 536/18.1; 536/18.2; 536/124; 536/127
(58) Field of Search .............. 536/18.6, 18.1, 536/18.2, 4.1, 124, 127

(56) References Cited

U.S. PATENT DOCUMENTS

| | | | |
|---|---|---|---|
| 3,408,441 A | 10/1968 | von Wartburg et al. | 424/180 |
| 3,524,844 A | 8/1970 | Keller-Juslen et al. | 260/210 |
| 4,564,675 A | 1/1986 | Kurabayashi et al. | 536/18.1 |
| 4,757,138 A | 7/1988 | Fujii et al. | 536/18.1 |
| 4,791,207 A | 12/1988 | Salzmann et al. | 548/110 |
| 4,997,931 A | 3/1991 | Ohnuma et al. | 514/27 |
| 5,206,350 A | 4/1993 | Wang et al. | 536/18.1 |
| 5,459,248 A | 10/1995 | Silverberg et al. | 536/18.6 |
| 5,688,925 A | 11/1997 | Allevi et al. | 536/186 |
| 5,688,926 A | 11/1997 | Silverberg et al. | 536/18.6 |

FOREIGN PATENT DOCUMENTS

| | | |
|---|---|---|
| EP | 778 282 A1 | 6/1997 |
| WO | WO 93/02094 | 2/1993 |

OTHER PUBLICATIONS

Allevi et al., "A Short and Simple Synthesis of the Antitumor Agent Etoposide," *Tetrahedron Letters* 33(33): 4831–4834, 1992.

Daley et al., "Synthesis and Antitumor Activity of New Glycosides of Epipodophyllotoxin, Analogues of Etoposide, and NK 611," *J. Med. Chem.* 41: 4475–4485, 1998.

*Primary Examiner*—Gary Geist
*Assistant Examiner*—Everett White
(74) *Attorney, Agent, or Firm*—SEED Intellectual Property Law Group PLLC

(57) ABSTRACT

A synthetic method for the preparation of the anti-tumor drug Etoposide. In one embodiment, the method includes the direct condensation of 4'-demethyl-epipodophylloxin with 2,3-di-O-dichloroacetyl-(4,6-O-ethylidene)-β-D-glucopyranose in the presence of trimethylsilyl trifluoromethane sulfonate (TMSOTf) to yield 4'-demethylepipodophyllotoxin-4-(2,3-di-O-dichloroacetyl-4,6-O-ethylidene)-β-D-glucopyranoside, followed by conversion of the same to etoposide. Other methods include use of different Lewis acids as catalyst, as well as different substituted glucopyranosides. This method provides enhanced yields over existing synthetic techniques, reduced reaction times and permits more favorable isolation reaction procedures.

36 Claims, No Drawings

SYNTHETIC METHOD FOR THE PREPARATION OF THE ANTINEOPLASTIC AGENT ETOPOSIDE

CROSS-REFERENCE TO RELATED APPLICATION

This application is a continuation of U.S. patent application Ser. No. 09/150,879, filed Sep. 10, 1998 now abandoned.

TECHNICAL FIELD

This invention is directed to an improved synthetic method for the preparation of etoposide, particularly in the context of improved yield, reduced reaction times and simplified isolation procedures.

BACKGROUND OF THE INVENTION

Etoposide is an antineoplastic agent having the following structure (1):

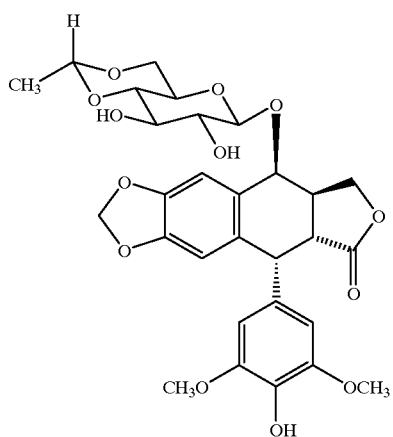

(1)

Etoposide has been used effectively as an anti-tumor drug for a variety of conditions. For example, it has been employed in the treatment of acute monocytic leukemia (Schilling's leukemia), as well as medullary monocytic leukemia, and has proved effective for the treatment of recticulum cell sarcoma, tissue-cellular lymphoma, lymphasarcoma and Hodgkin's disease. Due to the well recognized activity of etoposide, a number of techniques have been developed directed to its synthesis.

One synthetic technique is that reported by Kuhn et al. in Swiss Patent No. 514,578, and related techniques disclosed in U.S. Pat. Nos. 3,408,411 and 3,524,844. Kuhn et al. discloses the preparation of etoposide by the reaction of 4'-demethyl-epipodophyllotoxin (2) with chloroformic acid benzyl ester (as a protecting group for the 4'-phenolic alcohol) to give 4'-carbobenzoxy-4'-demethyl-epipodophyllotoxin (3), followed by reaction of (3) with 2,3,4,6-tetra-O-acetyl-β-D-glucose (4) in the presence of boron trifluoride diethyl etherate to give tetra-O-acetyl4'-carbobenzoxy-4'-demethyl-epipodophyllotoxin-β-D-glucoside (5):

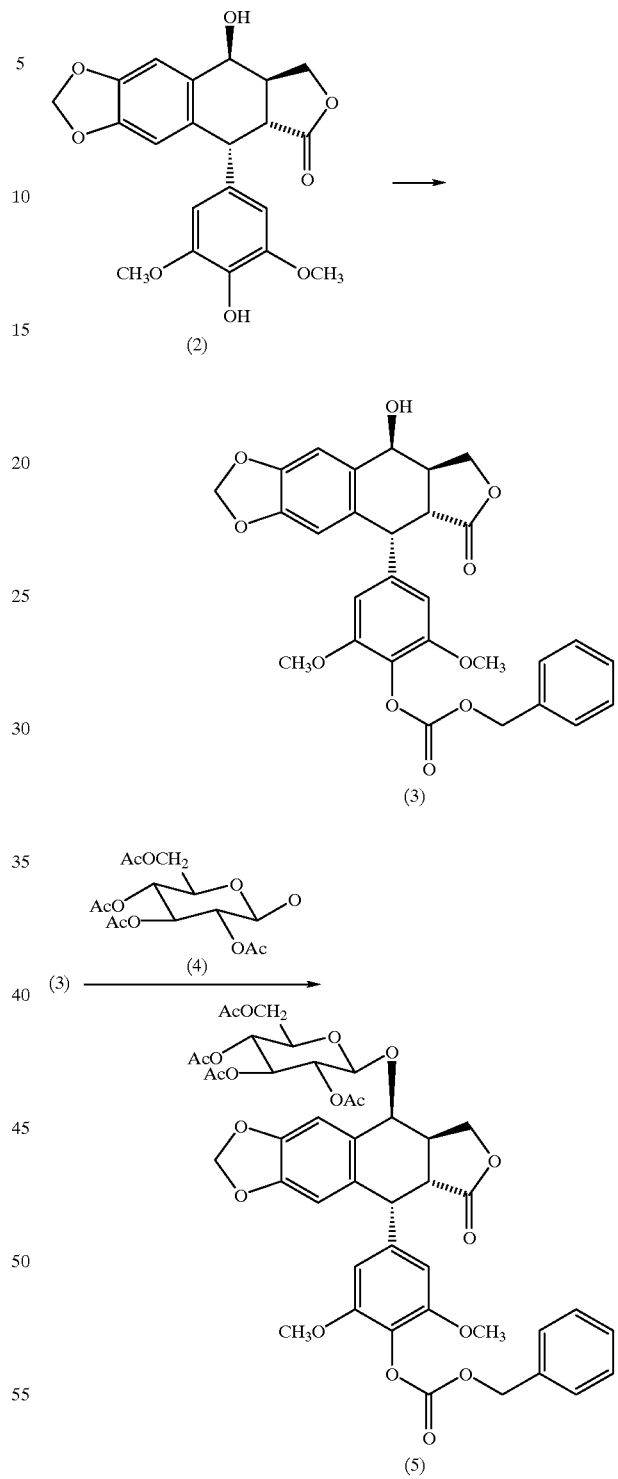

The carbobenzoxy protecting group of compound (5) is removed to give tetra-O-acetyl-4'-demethyl-epipodophyllotoxin-β-D-glucoside (6), which is then deacylated in the presence of zinc acetate to form 4'-demethyl-epipodophyllotoxin-β-D-glucoside (7):

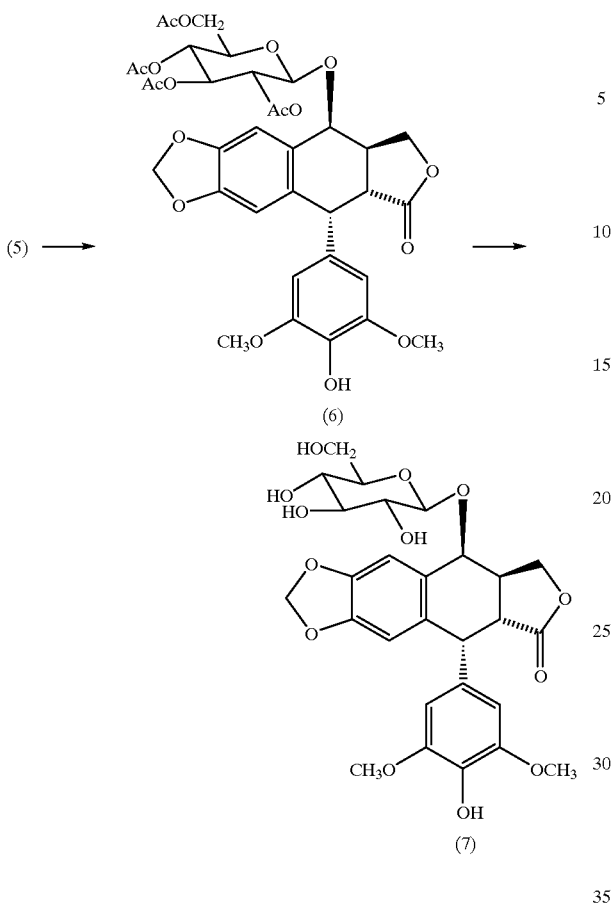

(5) →

(6)

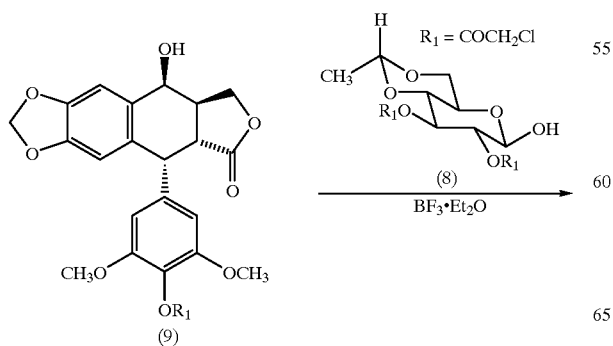

(7)

Conversion of 4'-demethyl-epipodophyllotoxin-β-D-glucoside (7) to etoposide is achieved by reacting with acetaldehyde-dimethylacetal and p-toluene sulphonic acid. This synthetic method, however, in addition to requiring numerous reaction steps, is of low yield. That is, only about 18% etoposide based on 4'-demethyl-epipodophyllotoxin (2).

Another synthetic method is disclosed by Kurabayashi and Kalsuhiko et al. in Japanese Patent No. 84/98098. Unlike the method of Kuhn et al., 2,3-di-O-chloroacetyl-(4,6-O-ethylidene)-β-D-glucopyranose (8)—as opposed to glucose (4) of Kuhn et al.—is reacted directly with a 4'-(protected)-4'demethyl-epipodophyllotoxin (9) in the presence of boron trifluoride etherate to give intermediate (10):

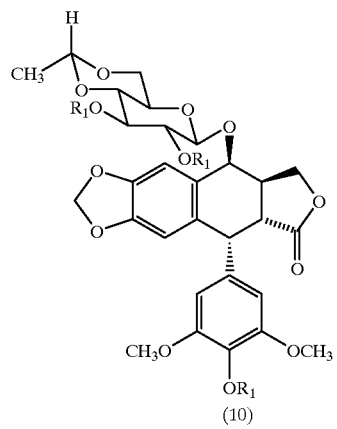

(10)

The resulting intermediate (10) is then converted to etoposide by reaction with zinc acetate. While this method represents an improvement of the technique of Kuhn et al., strict reaction conditions are required for controlling monoacylation of the 4'-phenolic hydroxyl group to generate compound (9) from 4'-demethyl-epipodophyllotoxin.

A further improvement to the synthesis of etoposide is disclosed in U.S. Pat. No. 5,206,350 by Wang et al. In that method, direct addition of 2,3-di-O-chloroacetyl-(4,6-O-ethylidene)-β-D-glucopyranose (8) to 4'-demethyl-epipodophyllotoxin (2) is achieved in the presence of boron trifluoride etherate as catalyst without having to employ a protecting group on the 4'-phenolic hydroxyl group, giving 4'-demethylepipodophyllotoxin4-(2,3-di-O-chloroacetyl-4,6-O-ethylidene)-β-D-glucopyranoside (11):

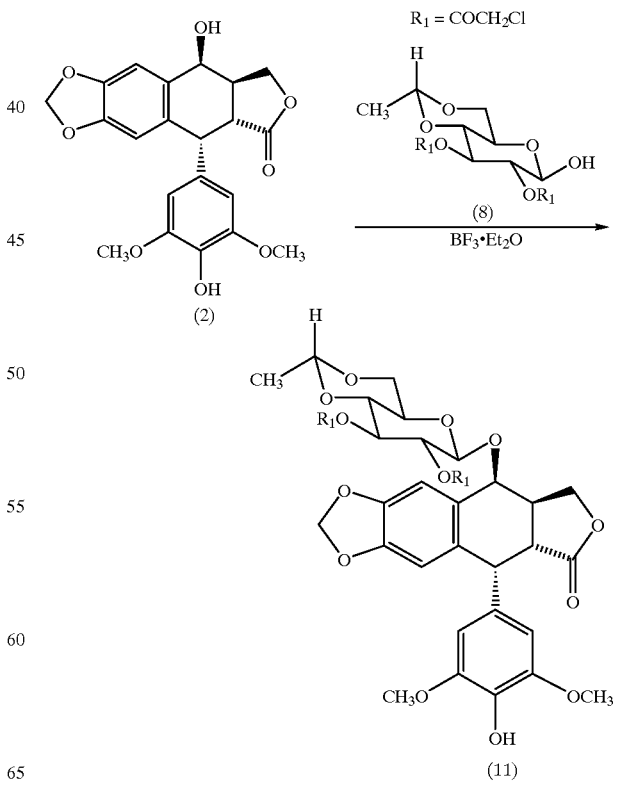

After removal of the chloroacetyl protecting groups from compound (11) with zinc acetate in methanol, etoposide is obtained at a reported yield of 54% (based on 4'-demethyl-epipodophyllotoxin).

While eliminating the need to protect the 4'-phenolic hydroxyl group of compound (2), Wang et al. still suffers drawbacks with regard to yield, extended reaction times and isolation methodology. Accordingly, there exists a need in the art for improved synthetic methods for making etoposide which overcome these deficiencies. The present invention fulfills these needs and provides further related advantages.

SUMMARY OF THE INVENTION

This invention is directed to an improved synthetic procedure for the synthesis of etoposide. Due to the well know utility of etoposide, particularly in the context of cancer treatment, synthetic methods which result in higher yields of etoposide are of particular interest, especially with regard to commercial manufacture of the same. The present invention provides a relatively simple method of making etoposide at higher yields than existing techniques, and under more favorable reaction times and much simplified isolation procedures.

In one embodiment, a method for making etoposide is disclosed comprising the steps of:

condensing 4'demethyl-epipodophyllotoxin of formula (2) with a glucopyranose of formula (13) in an organic solvent at a temperature below −30° C. and in the presence of trimethylsilyl triflate catalyst to give a compound of formula (14):

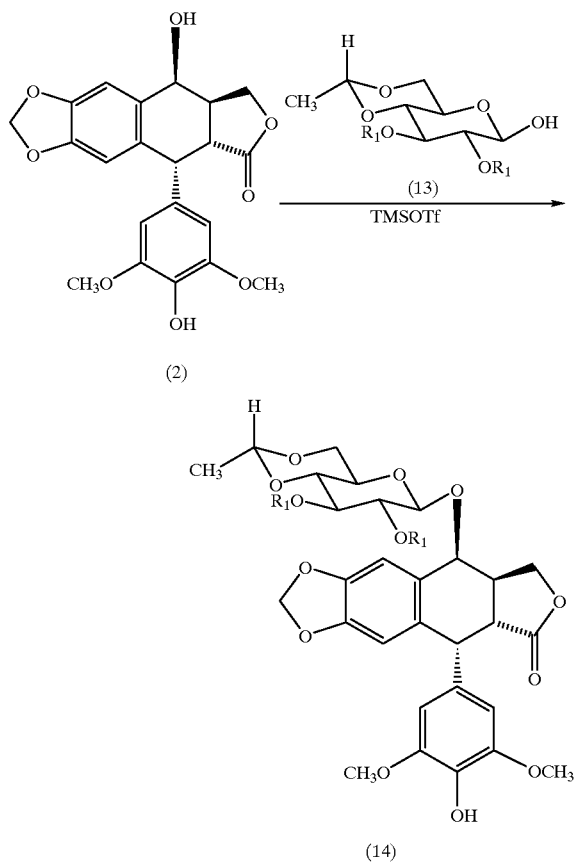

where $R_1$ is —$COCH_3$, —$COCH_2X$, —$COCHX_2$ or —$COCX_3$, and each occurrence of X is independently selected from a halogen; and converting compound (14) to etoposide (1) having the following formula:

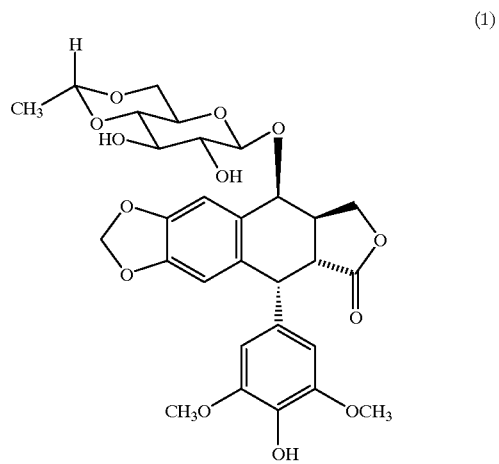

In more specific aspects of this embodiment, the compound of formula (13) is present in about 1.5 to about 2.0 equivalents based on the compound of formula (2), and trimethylsilyl triflate is present in about 1.5 to about 2.5 equivalents based on the compound of formula (2). Condensation of the compound of formula (13) and the compound of formula (2) is typically in the range from −40° C. to −60° C., and may be performed in the presence of a drying agent such as dry molecular sieve or zeolite. The organic solvent is typically a halogenated or non-halogenated organic solvent, including (but not limited to) acetonitrile, acetone, diethylether, chloroform, dichloromethane, 1,2-dichloroethane, or mixtures thereof. Preferred $R_1$ groups of the glucopyranose of formula (3) include —$COCHCl_2$ and —$COCH_2Cl$.

In the condensing step, the trimethylsilyl triflate may be added to the mixture of the compound of formula (13) and the compound of formula (2) over a period of about 30 minutes, with the temperature of the mixture being maintained at about −50° C. to about −40° C. The condensing step may be completed in about 1 to 2 hours.

In the converting step, such conversion may be accomplished by alcoholysis with, for example, a transesterification catalyst such as zinc acetate dihydrate. The zinc acetate dihydrate may be present in about 1.0 to about 2.0 equivalents based on the compound of formula (14). The converting step may be performed in the presence of an organic solvent, including (but not limited to) a $C_{1-4}$alkanol such as methanol. The compound of formula (14) and zinc acetate dihydrate may be heated to a temperature ranging from about 60° C. to about 75° C. for up to about 2 hours.

In a further embodiment, compound (14) may be eluted through a celite/basic alumina column, or a silica gel, prior to being converted to etoposide. In still a further embodiment, the resulting etoposide may be purified. Such purification may be accomplished by, for example, crystallization, extraction or column chromatography. Crystallization may be from a $C_{1-4}$alkanol, a $C_{1-4}$aliphatic ester, or a non-polar solvent, where the $C_{1-4}$alkanol includes methanol and ethanol, the $C_{1-4}$aliphatic ester includes ethyl acetate, and the non-polar solvent includes n-pentane or hexanes or petroleum ether. The temperature of such crystallization may be from −4° C. to 0° C. for 8 to 12 hours.

Preferably, the etoposide of this invention is at least 99% pure, is substantially free of a dimer of 4'demethyl-4-epipodophyllotoxin, and is substantially free of etoposide in the α-glucoside form. In this context, the term "substantially" means less than 0.5% by weight.

In another embodiment of this invention, a method for making etoposide is disclosed comprising the steps of:

condensing 4'-demethyl-epipodophyllotoxin of formula (2) with 2,3-di-O-dihaloacetyl-(4,6-O-ethylidene)-β-D-glucopyranose of formula (13) in an organic solvent at a temperature below −20° C. and in the presence of a Lewis acid catalyst to give 4'-demethylepipodophyllotoxin-4-(2,3-di-O-dihaloacetyl-4,6-O-ethyidene)-β-D-glucopyranoside of formula (14):

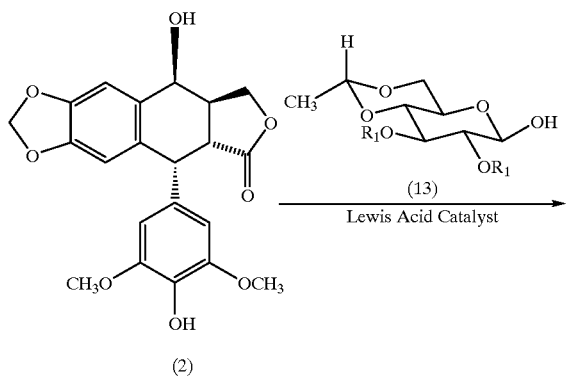

where $R_1$ is —COCHX$_2$ and each occurrence of X is independently selected from a halogen; and converting the 4'-demethylepipodophyllotoxin-4-(2,3-di-O-dihaloacetyl-4,6-O-ethylidene)-β-D-glucopyranoside of formula (14) to etoposide (1) having the following formula:

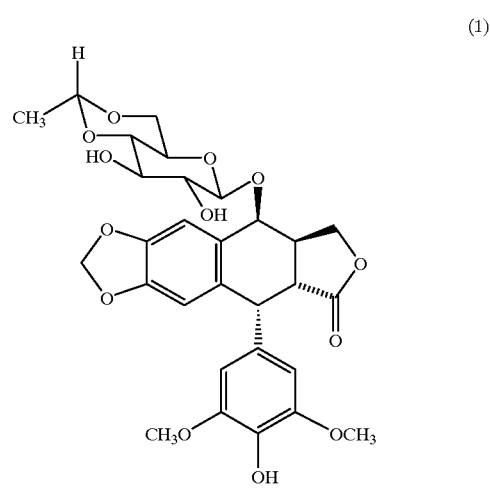

In more specific aspects of this embodiment, the Lewis acid may be a tri($C_{1-4}$alkyl)silyltrifluoromethane sulfonate, such as trimethylsilyl triflate, or a boron trifluoride di-$C_{1-4}$alkylether complex, such as boron trifluoride etherate. Further Lewis acids include (but are not limited to) $ZnCl_2$, DEAC, $CF_3SO_3H$ or $CF_3SO_3Ag$. A preferred $R_1$ for the 2,3-di-O-dihaloacetyl-(4,6-O-ethylidene)-β-D-glucopyranose of formula (13) is —COCHCl$_2$.

In still a further embodiment of this invention, a method for making etoposide is disclosed comprising the steps of:

condensing 4'-demethyl-epipodophyllotoxin of formula (2) with a glucopyranose of formula (13) in an organic solvent at a temperature below −20° C. and in the presence of a Lewis acid catalyst to give a compound of formula (14):

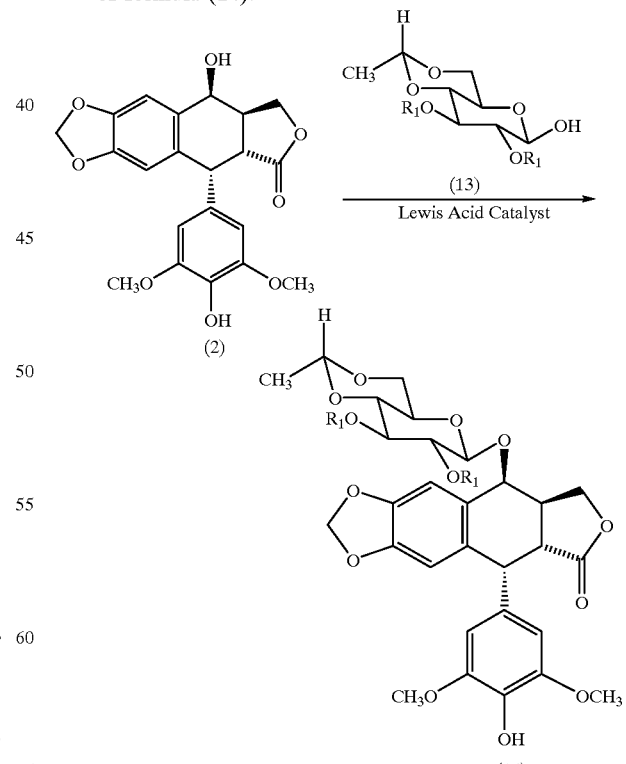

where R₁ is —COCH₃, —COCH₂X, —COCHX₂, or —COCX₃, and each occurrence of X is independently selected from a halogen;

collecting compound (14) by elution through a celite/ basic alumina column or silica gel; and converting the collected compound (14) to etoposide (1) having the following formula:

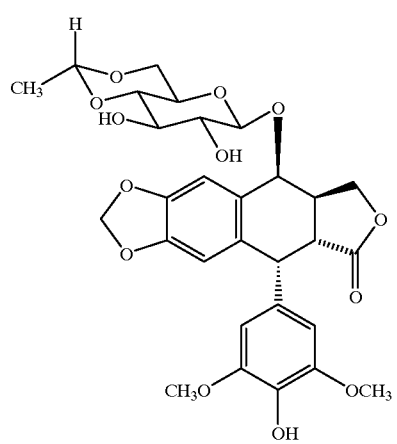

In more specific aspects of this embodiment, Lewis acid is a tri($C_{1-4}$alkyl)silyltrifluoromethane sulfonate, such as trimethylsilyl triflate, or a boron trifluoride di-$C_{1-4}$alkylether complex, such as boron trifluoride etherate. Further Lewis acids include (but are not limited to) $ZnCl_2$, DEAC, $CF_3SO_3H$ or $CF_3SO_3Ag$. A preferred $R_1$ for the glucopyranose of formula (13) is —COCHCl₂.

These and other aspects of this invention will be evident upon reference to the following detailed description.

DETAILED DESCRIPTION OF THE INVENTION

As mentioned above, this invention is directed to a method for making etoposide at high yield and under simplified reaction conditions. The method involves the direct condensation of 4'-demethyl-epipodophyllotoxin (2) with 2,3-di-O-dichloroacetyl-(4,6-O-ethylidene)-β-D-glucopyranose (13) in the presence of trimethylsilyl trifluoromethane sulfonate (TIMSOTf) to yield 4'-demethylepipodophylotoxin-4-(2,3-di-O-dichloroacetyl-4,6-O-ethylidene)-β-D-glucopyranoside (14) as represented by the following Reaction Scheme 1:

Reaction Scheme 1

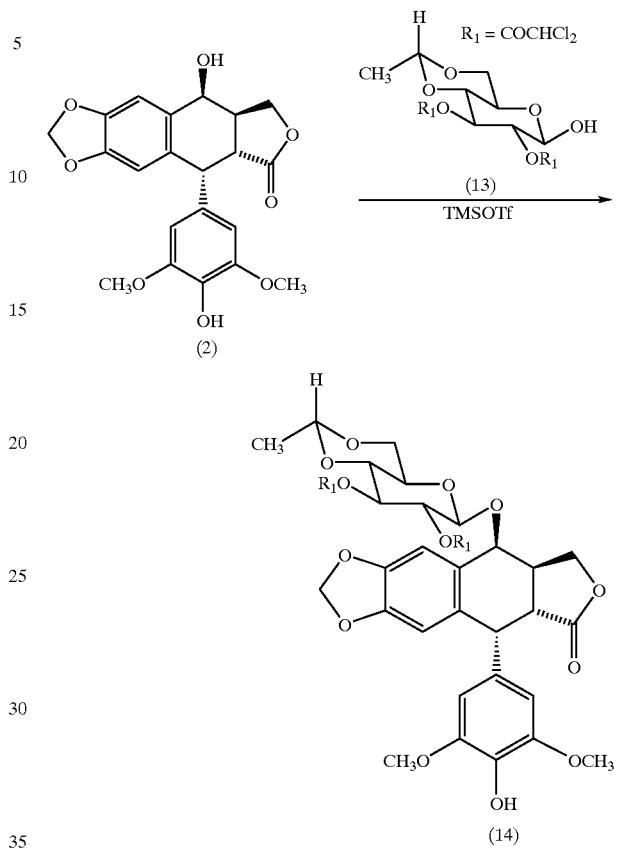

The above reaction is carried out at a temperature range of below −30° C. and generally in the range of −40° C. to −50° C., for a period of time ranging from 1 to 3 hours and typically from 1 to 2 hours. As with the prior technique of Wang et al., the condensation is performed without protecting the 4'-phenolic hydroxyl moiety of compound (2). However, unlike the prior technique, reaction product (14) may be collected by filtration through basic alumina, thereby avoiding the long isolation procedures reported by Wang et al. and Kuhn et al. For example, Kuhn et al. utilizes aqueous base treatment followed by repeated extractions with an organic solvent, and successive washings with hydrochloric acid solution, $NaHCO_3$, water and drying over anhydrous sodium sulfate. Such a long work-up methodology generally leads to the formation of undesired side-products, which are avoided in the simplified isolation procedures of the present invention.

Regeneration of the alcoholic group at the 2- and 3-positions of the glycosidic moiety of compound (14) may be accomplished by alcoholysis using zinc acetate dihydrate. The resulting product of this transesterification reaction is etoposide (1).

In Reaction Scheme 1 above, 4'-demethyl-epipodophylloxin (2) may be obtained from podophyllotoxin by, for example, the techniques disclosed in U.S. Pat. No. 3,524,844 to Kuhn et al. (incorporated herein by reference). Further, 2,3-di-O-dichloroacetyl-(4,6-O-ethylidene)-β-D-glucopyranose (13) may be prepared from 2,3-di-O-dichloroacetyl-1-O-benzyloxycarbonyl-(4,6-O-ethylidene)-β-D-glucopyranose (12) by hydrogenolysis using 10% palladium on activated carbon.

Thus, the overall reaction for synthesis of etoposide by the method of this invention may be represented by the following Reaction Scheme 2:

A number of advantages are associated with the present invention. For example, this synthetic technique is a highly efficient process, wherein all reactions may be carried out within 1–2 hours, and providing much simplified isolation procedures. Protection of the 4'-phenolic group of starting compound (2) is avoided, and no purification is involved in the individual steps, with only the final product being re-crystallized once. Further, all reactions are readily monitored by thin layer chromatography. Lastly, and perhaps most importantly, the overall yield is significantly higher that existing synthetic techniques.

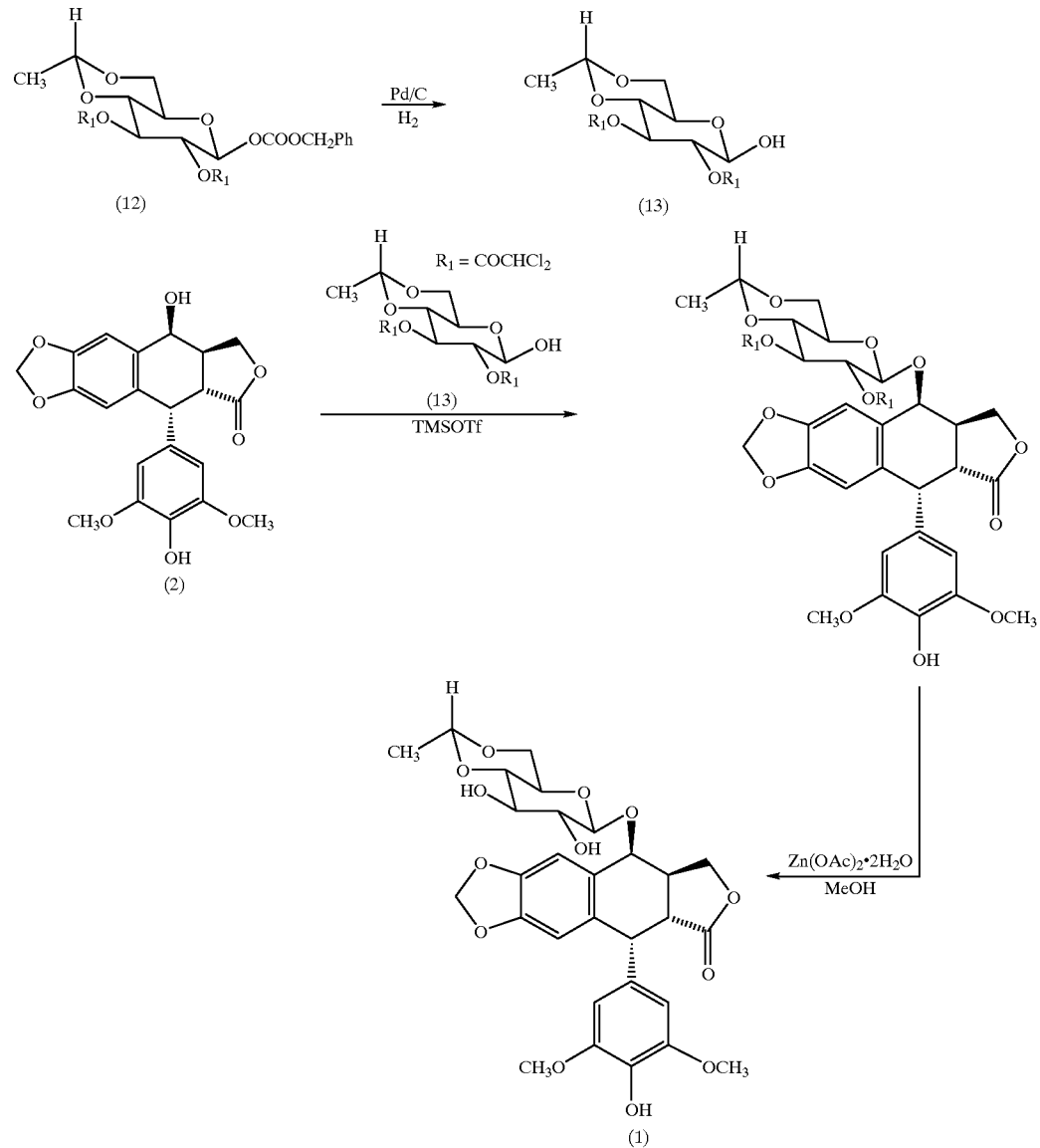

Reaction Scheme 2

In an alternative embodiment of this invention, the $R_1$ groups of glucopyranose (13) may be —COCH$_3$, —COCH$_2$X, —COCHX$_2$ or —COCX$_3$, where each occurrence of X is independently selected from a halogen. In a preferred embodiment, as represented by Reaction Schemes 1 and 2 above, $R_1$ is —COCHCl$_2$. However, in other embodiments suitable $R_1$ moieties include —COCH$_2$Cl and —COCH$_2$Br, as well as the other $R_1$ moieties noted above.

Presently, the best synthetic method for making etoposide is the technique disclosed above by Wang et al. In that technique, the overall yield of etoposide—calculated based on compound (2)—was 54%. In contrast, utilizing trimethylsilyl triflate as the catalyst, the overall yield of etoposide according to the method of the present invention is about 68%—again, based on compound (2). This represents a 25% increase in yield over Wang et al. Furthermore, the present invention provides new isolation conditions for the intermediate (14), thus eliminating the formation of further side-products and any epimerized side-products.

It should be recognized that the technique of Wang et al. employs boron trifluoride etherate as the catalyst for formation of 4'-demethylepipodophyllotoxin-4-(2,3-di-O-chloroacetyl-4,6-O-ethylidene)-β-D-glucopyranoside (11) by the direct condensation 2,3-di-O-chloroacetyl-(4,6-O-ethylidene)-β-D-glucopyranose (8) with 4'-demethyl-epipodophyllotoxin (2). While boron trifluoride etherate of Wang et al. and others, and trimethylsilyl trifluoromethane sulfonate of the present invention may both be classified as Lewis acids, it has been surprisingly found that trimethylsilyl trifluoromethane sulfonate works significantly better than boron trifluoride etherate, as well as significantly better than other Lewis acids tested, including DEAC, $ZnCl_2$, $CF_3SO_3H$ and $CF_3SO_3Ag$.

While not intending to be limited by the following, it is believed that trimethylsilyl trifluoromethane sulfonate may function by a different mechanism than that of boron trifluoride etherate. The latter is believed to generate a carbocation intermediate at the C4 position of the aglucone, which is then attacked by the free hydroxyl group of the glucopyranose. In contrast, trimethylsilyl triflate apparently reacts with the free hydroxyl group of the glucopyranose to form a good leaving group, which facilitates the later attachment of the lignan moiety to give compound (14) with retention of stereochemistry that is the same as that of the starting materials. Furthermore, the use of trimethylsilyl triflate allows for a more efficient coupling, which results in 80% yield from lignan (2) to compound (14)—based on the lignan (2)—which is achieved within 2 hours, as opposed to only about 60% yield by Wang et al. Therefore, by use of trimethylsilyl triflate, significant advantages are achieved, including increased yield and reduced reaction times.

Furthermore, when the present invention employs boron trifluoride etherate as catalyst (the same catalyst disclosed by Wang et al.), improved yields are again obtained, that is, 60% yield compared to the 54% of Wang et al. This difference in yield is believed due to the use of a different glucopyranose (where $R_1$ is —$COCHCl_2$, rather than —$COCH_2Cl$ of Wang et al.), as well as being attributable to the simplified isolation procedures of this invention.

In addition to trimethylsilyl trifluoromethane sulfonate and boron trifluoride etherate, other. Lewis acids may, be employed, provide compound (14 is collected by elution through a celite/basic alumina column or a silica gel prior to converting the collected compound (14) to etoposide (1).

The following examples are presented by way of illustration, not limitation.

EXAMPLES

Example 1

PREPARATION OF 2,3-DI-O-DICHLOROACETYL-(4,6-O-ETHYLIDENE)-β-D-GLUCOPYRANOSE (HYDROGENOLYSIS) (13)

An over-dried 100 mL three-necked round bottom flask fitted with a stir bar, low temperature thermometer, septa and $H_2$ inlet was charged with 2,3-Di-O-dichloroacetyl-1-O-benzyloxycarbonyl-(4,6-O-ethylidene)-β-D-glucopyranose (1.8 mmol), in acetone (15–30% concentration) and 10% palladium on activated carbon powder (0.2 mmol). The solution was stirred until uniform and then cooled to –10° C. to 0° C. After the reaction was over the catalyst was filtered over sintered glass containing a plug of celite under reduced pressure. The sintered glass is washed trice with one times the total reaction volume of anhydrous acetone and the filtrates are pooled and then concentrated to dryness under reduced pressure at a temperature close to 30° C. The crude residue was dried under vacuum at ambient temperature and compound (13) was thus obtained as white foam in 98% yield with a melting point of 130–132° C. (from acetone). DCI-MS: 428; IR:$v_{max}$ $CHCl_3$: 3650, 1770, 1390, 1200 and 1100 $cm^{-1}$.

Example 2

PREPARATION OF 4'-DEMETHYL-EPI-PODOPHYLLOTOXIN-4-(2,3-DI-O-DICHLOROACETYL-4,6-O-ETHYLIDENE)-β-D-GLUCOPYRANOSIDE (14)

An oven-dried, three-neck 250 mL round bottom flask was fitted with a stir bar, low temperature thermometer, septa and argon inlet, was introduced with 4'-demethyl-epi-podophyllotoxin (2) (1 mmol), dry molecular sieve (¹⁄₁₆Δ pellets) and anhydrous dichloromethane (20–50% concentration). 2-3-Di-O-dichloroacetyl-(4,6-O-ethylidene)-β-D-glucopyranose (13) (1.7 mmol) in dichloromethane (10–20% concentration) was added via double-ended needle. The suspension was stirred until homogenous and then cooled to –40° C. to –60° C. in an atmosphere of argon and in the absence of moisture. To the stirred suspension was added via a syringe, trimethylsilyl trifluoromethane sulfonate (2 mmol) over 30 minutes. The reaction was held at between –50° C. and 40° C. for 30 minutes. The course of the coupling reaction was monitored by thin layer chromatography. The suspension was allowed to warm to about –30° C. and filtered through a short celite/basic alumina column, eluting twice with one times the total reaction volume of dichloromethane. The pooled filtrate was evaporated under reduced pressure to yield the crude intermediate product (14) (80% based on the lignan (2)). This crude product is used directly in the next step without any purification. A sample was purified by the chromatraton for spectroscopic identification. The results are as follows: m.p: 242–243° C. (from methanol); DCI-MS: 810.

Example 3

PREPARATION OF 4-DEMETHYL-EPI-PODOPHYLLOTOXIN-4-(4,6-O-ETHYLIDENE)-β-D-GLUCOPYRANOSE (ETOPOSIDE)

To 0.8 mmol of 4'-demethyl-epi-podophyllotoxin-4-(2,3-di-O-dichloroacetyl-4,6-O-ethylidene)-β-D-glucopyranose (14) in 10–25% concentration in methanol is added 1.5 mmol of zinc acetate dihydrate. The reaction mixture is refluxed with stirring under heating for 90 minutes. After completion of the reaction, the mixture is cooled and the volume reduced to one third by rotary evaporation under reduced pressure. Working up is effected by diluting the reaction solution with 100 mL dichloromethane and 100 mL of water. The aqueous phase was washed with 50 mL of dichloromethane. The combined dichloromethane phases was washed twice with 50 mL water. 15 mL of methanol was added to the first wash to prevent precipitation of etoposide. The organic phase was dried over anhydrous sodium sulphate, filtered and concentrated by evaporation under vacuum to an amorphous solid. This solid was re-crystallized from methanol/n-pentane at –4° C. to 0° C., thus obtaining colorless amorphous powder of Etoposide (68% yield based on the lignan (2), if the mother liquors are treated the yield will be higher). m.p: 256–258° C.; DCI-MS:588.

Example 4

PREPARATION OF ETOPOSIDE EMPLOYING 2,3-DI-O-DICHLOROACETYL-(4,6-O-ETHYLIDENE)-β-D-GLUCOPYRANOSE AND BORON TRIFLUORIDE ETHERATE AS CATALYST

4'-demethyl-epi-podophyllotoxin (1 mmol) and 2,3-di-O-dichloroacetyl-(4,6-O-ethylidene)-β-D-glucopyranose (2 mmol) were introduced into dry dichloromethane (20–50% concentration based on the lignan) under anhydrous condition. When the temperature was stabilized to –20° C. to –30° C., boron trifluoride etherate (1.5 mmol) was added slowly with stirring. Reaction was continued at this temperature and monitored by thin layer chromatography. After the completion of the reaction as evidenced by TLC, the solution was washed with water, dried over anhydrous sodium sulfate and concentrated under reduced pressure to afford the crude intermediate product (14). This crude product was then converted to etoposide by following the procedure as outlined in Example 3. The yield of final product etoposide was about 60% based on the lignan.

It will be appreciated that, although specific embodiments of the invention have been described herein for purpose of illustration, various modifications may be made without departing from the spirit and scope of the invention. Accordingly, the invention is not limited except as by the appended claims.

I claim:

1. A method for making etoposide, comprising the steps of:

condensing 4'-demethyl-epipodophyllotoxin of formula (2) with a glucopyranose of formula (13) in an organic solvent at a temperature below –30° C. and in the presence of trimethylsilyl triflate catalyst (TMSOTf), to give a compound of formula (14):

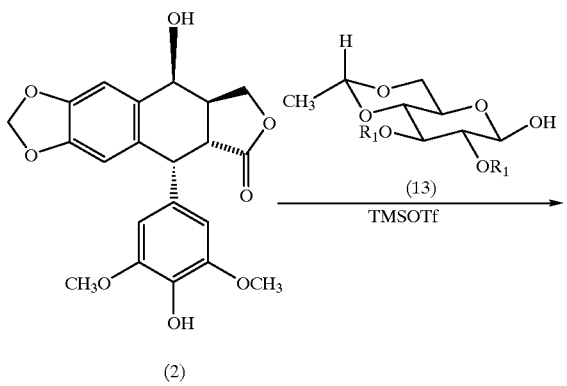

(2)

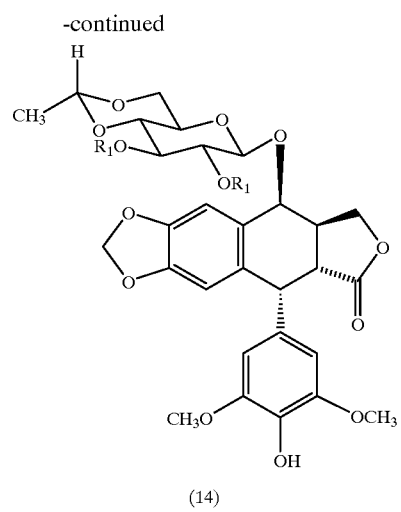

(14)

where $R_1$ is —$COCH_3$, —$COCH_2X$, —$COCHX_2$, or —$COCX_3$, and each occurrence of X is independently selected from a halogen; and converting compound (14) to etoposide having the following formula (1):

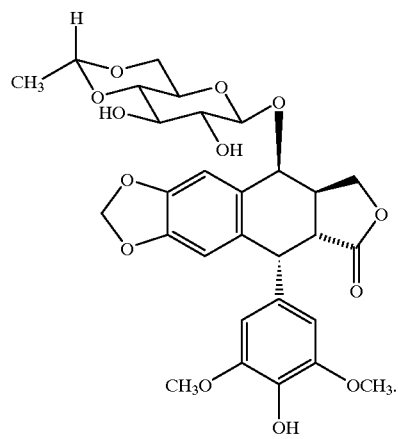

(1)

2. The method of claim 1 wherein the compound of formula (13) is present in about 1.5 to about 2.0 equivalents based on the compound of formula (2).

3. The method of claim 1 wherein trimethylsilyl triflate is present in about 1.5 to about 2.5 equivalents based on the compound of formula (2).

4. The method of claim 1 wherein the compound of formula (13) and the compound of formula (2) are condensed at a temperature ranging from –40° C. to –60° C.

5. The method of claim 1 wherein the step of condensing is performed in the presence of a drying agent.

6. The method of claim 5 wherein the drying agent is a dry molecular sieve or zeolite.

7. The method of claim 1 wherein the organic solvent is a halogenated or non-halogenated organic solvent.

8. The method of claim 7 wherein the solvent is acetonitrile, acetone, diethylether, chloroform, dichloromethane, 1,2-dichloroethane, or mixtures thereof.

9. The method of claim 7 wherein the solvent is dichloromethane.

10. The method of claim 1 wherein, during the condensing step, the trimethylsilyl triflate is added to a mixture of the compound of the formula (13) and the compound of formula (2) over a period of about 30 minutes, with the temperature of the mixture being maintained at about −50° C. to about −40° C.

11. The method of claim 1 wherein the condensing step is completed in about 1 to 2 hours.

12. The method of claim 1 wherein compound (14) is eluted through a celite/basic alumina column prior to being converted to etoposide.

13. The method of claim 1 wherein compound (14) is eluted through a silica gel-prior to being converted to etoposide.

14. The method of claim 1 wherein $R_1$ is —COCHX$_2$.

15. The method of claim 14 wherein $R_1$ is —COCHCl$_2$.

16. The method of claim 1 wherein $R_1$ is —COCH$_2$X.

17. The method of claim 16 wherein $R_1$ is —COCH$_2$Cl.

18. The method of claim 1 wherein the step of converting compound (14) to etoposide is accomplished by alcoholysis.

19. The method of claim 18 wherein alcoholysis is performed by contacting compound (14) with a transesterification catalyst.

20. The method of claim 19 wherein the transesterification catalyst is zinc acetate dihydrate.

21. The method of claim, 20 wherein the zinc acetate dihydrate is present in about 1.0 to about 2.0 equivalents based on the, compound of formula (14).

22. The method of claim 20 wherein the compound of formula (14) and zinc acetate dihydrate are heated to a temperature ranging from about 60° C. to about 75° C. for up to about 2 hours.

23. The method of claim 1 wherein the step of converting compound (14) to etoposide is performed in the presence of an organic solvent.

24. The method of claim 23 wherein the solvent is a $C_{1-4}$alkanol.

25. The method of claim 24 wherein the $C_{1-4}$alkanol is methanol.

26. The method of claim 1, further comprising the step of purifying the resulting etoposide (1).

27. The method of claim 26 wherein purification is by crystallization, extraction or column chromatography.

28. The method of claim 26 wherein purification is by crystallization from a $C_{1-4}$alkanol, a $C_{1-4}$aliphatic ester, or a non-polar solvent.

29. The method of claim 28 wherein the $C_{1-4}$alkanol is methanol or ethanol.

30. The method of claim 28 wherein the $C_{1-4}$aliphatic ester is ethyl acetate.

31. The method of claim 28 wherein the non-polar solvent is n-pentane or hexanes or petroleum ether.

32. The method of claim 28 wherein the temperature of crystallization is −4° C. to 0° C.

33. The method of claim 28 wherein the time for crystallization is 8 to 12 hours.

34. The method of claim 26 wherein, the purified etoposide is at least 99% pure.

35. The method of claim 26 wherein the purified etoposide is substantially free of a dimer of 4'demethyl-4-epipodophyllotoxin.

36. The method of claim 26 wherein the purified etoposide is substantially free of etoposide in the α-glucoside form.

* * * * *